United States Patent [19]
Itoh

[11] Patent Number: 5,649,908
[45] Date of Patent: Jul. 22, 1997

[54] DILATATION CATHETER

[75] Inventor: Takao Itoh, Machida, Japan

[73] Assignee: Yugengaisha New-Wave Medical, Tokyo, Japan

[21] Appl. No.: 667,045

[22] Filed: Jun. 20, 1996

[30] Foreign Application Priority Data

Jun. 23, 1995 [JP] Japan .................... 7-157715

[51] Int. Cl.6 .................................................. A61M 25/00
[52] U.S. Cl. ................................................ 604/96; 604/103
[58] Field of Search ........................ 604/96, 280, 283, 604/264, 97–103; 606/192–194

[56] References Cited

U.S. PATENT DOCUMENTS

| | | |
|---|---|---|
| 4,917,666 | 4/1990 | Solar et al. . |
| 4,960,410 | 10/1990 | Pinchuk . |
| 5,522,800 | 6/1996 | Crocker ........................ 604/96 |
| 5,569,200 | 10/1996 | Umeno et al. .................. 604/96 |
| 5,575,772 | 11/1996 | Lennox ........................ 604/96 |

*Primary Examiner*—John D. Yasko
*Attorney, Agent, or Firm*—Greenblum & Bernstein P.L.C.

[57] ABSTRACT

In the catheter comprising: a balloon 11 provided with a front and a rear opening end and a thin wall made of synthetic resins; an outer tube 21; an inner tube 31 which is disposed inside the outer tube 21 and has its tip portion projected outward from the outer tube 21; and, the balloon 11 having the front and the rear opening end fixedly mounted in a water-tight manner on the inner tube 31 and the outer tube 21 to form a front fixed portion 61 and a rear fixed portion 61', respectively;

a plurality of parallel-extending circumferential grooves 41 are provided to a distal area 32 of the inner tube 31, each of the circumferential grooves 41 having a predetermined length, and said distal area having a certain length which extends from said front fixed portion and over said rear fixed portion in a direction of the hub portion.

10 Claims, 4 Drawing Sheets

DILATATION CATHETER

BACKGROUND OF THE INVENTION

1. Field of the Invention

The present invention relates to a dilatation catheter for use in medical procedures such as PTCA (i.e., Percutaneous Transluminal Coronary Angioplasty) operation and the like, the catheter also being used for dilatation (i.e., widening in diameter of the passageway) of a stenotic lesion of a tubular organ such as blood vessels and the like.

2. Description of the Prior Art

When a deposit called atheroma appearing in an inner peripheral wall of a coronary artery through which the blood is supplied to the heart muscles grows in gravity, i.e., a so-called atherosclerosis becomes serious, the amount of the blood to be supplied to the heart muscles decreases, which increases the potential for angina pectoris or cardiac infarction.

In order to cure the atherosclerosis, a drug is administered. In addition to this, in case that the disease is serious, the PTCA, i.e., operation for dilatation of the coronary artery is conducted.

In the PTCA, as shown in FIG. 8, a pipe-like guiding catheter 100 is introduced from the root of a patient's thigh into his body to have its tip portion reach an coronary inlet portion 301 of a coronary artery 300 through a cardiac aorta 200 and engage with the inlet portion 301. A catheter assembly 1, which is provided with a balloon 11 in its front-end portion, is introduced into the patient's body by using a guide wire 500 through the guiding catheter 100. Then, at first, a front-end portion of the guide wire 500 is passed through the coronary inlet portion 301 and a stenotic lesion 400 of the coronary artery, and temporarily fixed there. After that, the catheter assembly 1 is followed to the guide wire 500 and introduced into the coronary artery 300 from its inlet portion 301 to reach the stenotic lesion 400 of the artery 300 so that the balloon 11 is located in the stenotic lesion 400. Under such circumstances, the balloon 11 is inflated with a radiopaque dye to exert an expanding pressure on the stenotic lesion 400 of the coronary artery 300, in which the deposit called atheroma is located, so that the stenotic lesion 400 is forcibly opened to allow the blood to pass therethrough.

More specifically, the catheter assembly 1 is constructed of the balloon 11 in distal-end portion, a hub in proximal-end portion, an outer tube and an inner tube which is provided inside the outer tube in a condition in which the inner tube has its tip portion projected outward from the outer tube. The balloon 11 has a front and a rear opening portion thereof fixedly mounted on an outer peripheral surface of the inner tube and that of the outer tube in the vicinities of front-end portions of these tubes, respectively. The balloon 11 is made of PE (i.e., polyethylene) resins or PET (i.e., polyethylene terephthalate) resins to assume a thin-walled one. In use, the balloon 11 wrapped around the inner tube of the catheter assembly 1 is under negative pressure and inserted into the guiding catheter 100 in its wrapped condition.

However, the inner tube made of plastic resins and provided with the balloon 11 is too small in diameter, and, therefore tends to be kinked at the same portion in operation when it is passed through a bent portion of the guiding catheter 100 or that of the coronary artery 300 or when it hits against the stenotic lesion 400, which makes it hard for the inner tube of the catheter assembly 1 to pass through the stenotic lesion 400. Further, there is a fear that the coronary artery 300 and the stenotic lesion 400 are damaged to cause a fatal accident during the above operation. In order to avoid such accident, the catheter assembly 1 is frequently replaced with a new one in the same operation, which takes to much time and labor.

After completion of the operation, the catheter assembly 1 is pulled out of the guiding catheter 100 in a condition in which the balloon 11 is deflated by drawing off the radiopaque dye.

However, in case that the balloon 11 is made of PET (i.e., polyethylene terephthalate) resins, when the balloon 11 is deflated, it assumes a flatfish-like shape having a wide slightly larger than a diameter of the inflated balloon 11 without shrinking in size due to its poor resiliency in contrast with PE (i.e., polyethylene) resins. Such flatfish-like shape of the deflated balloon 11 makes it sometimes hard to pull the balloon 11 out of the guiding catheter 100 due to frictional resistance therebetween, and even makes it impossible to push and pull the catheter assembly 1 in the coronary artery 300, which may damage an inner wall of the coronary artery 300 and also damage the balloon 11 in an inlet portion of the guiding catheter 100.

SUMMARY OF THE INVENTION

Under such circumstances, the present invention was made. Therefore, it is an object of the present invention to provide a dilatation catheter used in the PTCA (i.e., Percutaneous Transluminal Coronary Angioplasty) operation, which advances cross-ability of a stenotic lesion in a coronary artery, the catheter permitting its distal area of the inner tube to resiliently and flexibly change its shape when the inner tube hits the stenotic lesion in the coronary artery and is prevented from moving ahead, which increases the potential of a distal portion of the catheter to pass through the stenotic lesion without kinking the inner tube of the catheter assembly and without increasing frictional resistance between an inner wall of the coronary artery and the distal portion of the catheter.

It is another object of the present invention to provide a dilatation catheter used in the PTCA operation, the catheter assembly being provided with a balloon made of PET (i.e., polyethylene terephthalate) resins and permitting the balloon to shrink in diameter without assuming a flatfish-like shape when a radiopaque dye is pulled out of the balloon after completion of the PTCA operation.

According to a first aspect of the present invention, the above object of the present invention is accomplished by providing:

In a dilatation catheter comprising:

a balloon provided with a front and a rear opening end and a thin wall made of synthetic resins;

an outer tube;

an inner tube which is disposed inside the outer tube and has its tip portion projected outward from the outer tube;

a hub portion; and the balloon having the front and the rear opening end fixedly mounted in a water-tight manner on the inner tube and the outer tube to form a front and a rear fixed portion, respectively;

the improvement wherein:

a plurality of parallel-extending circumferential slits or grooves are provided to a distal area of the inner tube, each of the circumferential slits or grooves having a predetermined length, and said distal area having a certain length which extends from said front fixed portion and over said rear fixed portion in a direction of the hub portion.

In action: in the dilatation catheter according to the first aspect of the present invention, since the inner tube of the catheter assembly has a plurality of parallel-extending circumferential grooves, there is no fear that the inner tube is permanently kinked at the distal area even when the catheter assembly passes through a bent portion of a guiding catheter or a severely curved of the coronary artery. When the inner tube is permanently kinked, its frictional resistance increases, so that cross-ability of the catheter in a stenotic lesion is dramatically dropped. According to the first aspect of the present invention, it is possible to insert the dilatation catheter into the patient's body in an easy manner.

In effect: the dilatation catheter according to the first aspect of the present invention is advantages in that, since the parallel-extending circumferential grooves each of which has a predetermined length are provided in the distal area of the inner tube to enable the inner tube to resiliently change its shape, there is no fear that the inner tube is permanently kinked when the catheter assembly passes through both the guiding catheter and the winding coronary artery and even when the inner tube hits against the stenotic lesion in the coronary artery.

Consequently, there is no fear that the inner tube is permanently kinked in a push and pull operation of the catheter assembly and the thus formed kink portion of the inner tube loses forward pushing energy of the catheter and the catheter may fail to cross the stenotic lesion of the artery.

According to a second aspect of the present invention, the above object of the present invention is accomplished by providing:

A dilatation catheter comprising:

a balloon provided with a front and a rear opening end and a thin wall made of polyethylene terephthalate resins;

an outer tube;

an inner tube which is disposed inside the outer tube and has its tip portion projected outward from the outer tube;

a hub portion;

the balloon having the front and the rear opening end fixedly mounted in a water-tight manner on the inner tube and the outer tube in a condition in which the balloon is axially stretched to form a front and a rear fixed portion, respectively; and a plurality of parallel-extending circumferential slits or grooves provided to a distal area of the inner tube, each of the circumferential slits or grooves having a predetermined length, and said distal area having a certain length which extends from said front fixed portion and over said rear fixed portion in a direction of the hub portion.

In action: in the dilatation catheter according to the second aspect of the present invention, as is in the catheter according to the first aspect of the present invention, there is no fear that the inner tube is permanently kinked. Further, in the catheter according to the second aspect of the present invention, the balloon made of the PET resins has a small diameter in a condition in which the balloon is axially stretched relative to the inner tube, so that the balloon is folded small naturally when the balloon is deflated.

Further, it is possible for the dilatation catheter according to the second aspect of the present invention to smoothly position the balloon in the stenotic lesion of the coronary artery as is in the dilatation catheter according to the first aspect of the present invention, and also possible to smoothly pull the catheter assembly out of the patient's body after completion of the operation.

Further, since the inner tube is resiliently and flexibly deformed in the balloon due to the provision of the circumferential grooves, there is no fear that the inner tube adversely affects inflation of the balloon.

In effect: since the balloon made of PET resins is fixed to the inner tube and the outer tube in the condition of axially stretched, it is possible for the balloon to return in small-diameter shape, not in flatfish shape, when the radiopaque dye is removed from the balloon, which enables the catheter assembly to be smoothly pulled out of the guiding catheter after completion of the operation for widening in diameter the passageway of the stenotic lesion in the coronary artery.

Further, it is possible for the dilatation catheter according to the second aspect of the present invention to conduct the above operation in safety using the same catheter assembly without replacing it with a new one.

According to a third aspect of the present invention, the above object of the present invention is accomplished by providing:

The dilatation catheter as set forth in the first or the second aspect of the present invention, wherein:

the parallel-extending circumferential slits or grooves are provided also in the remaining area of the inner tube or also in the outer tube in addition to a distal area of the inner tube.

In action: in the dilatation catheter according to the third aspect of the present invention, since the circumferential grooves are provided over the entire length of the inner tube, it is possible for the catheter assembly to smoothly pass through both the guiding catheter and the winding coronary artery in an easy manner. It is also possible to gradually reduce an axial interval between adjacent ones of the circumferential grooves as the circumferential grooves are spaced apart from each other forward in the inner tube, which enables the catheter assembly to be more smoothly operated or more resiliently deformed.

In effect: since the inner tube is resiliently deformed over its entire length, it is possible for the catheter assembly to pass through the guiding catheter in an easier manner. In other words, the doctor may operate the catheter assembly in an easier manner. Further, since the catheter assembly may smoothly track and pass though the winding portions and stenotic lesions of the coronary artery, there is no fear that the catheter assembly damages the coronary artery, which improves the dilatation catheter of the present invention in safety.

According to a fourth aspect of the present invention, the above object of the present invention is accomplished by providing:

The dilatation catheter as set forth in any one of the first, second and the third aspects of the present invention, wherein:

the distal area of the inner tube assumes a slightly curved shape.

In action: in the dilatation catheter according to the fourth aspect of the present invention, the distal area of the inner tube assumes a slightly curved shape, which further facilitates pushing and pulling the catheter assembly in both the guiding catheter and the coronary artery in operation and also facilitates resilient deformation of the inner tube so as to facilitate inflating the balloon made of PET resins.

In effect: since the inner tube provided with the circumferential grooves assumes a slightly curved shape, the inner tube may resiliently change its shape in an easy manner, which facilitates positioning the balloon in the passageway of the stenotic lesion in the coronary artery and also facilitates inflating the balloon made of PET resins in the operation to widen in diameter the passageway of the stenotic lesion in the coronary artery in a steady manner.

According to a fifth aspect of the present invention, the above object of the present invention is accomplished by providing:

The dilatation catheter as set forth in any one of the first, second, third and the fourth aspects of the present invention, wherein:

each of the inner tube and the outer tube is made of metals or rigid plastics which are not kinked.

According to a sixth aspect of the present invention, the above object of the present invention is accomplished by providing:

The dilatation catheter as set forth in any one of the first, second, third, fourth and the fifth aspects of the present invention, wherein:

a pair of the parallel-extending circumferential slits or grooves are oppositely disposed from each other on the same diameter.

Incidentally, fixed portions both the balloon and the tubes are made of synthetic resins such as polyethylene and the like through a thermocompression bonding process, an ultrasonic bonding process, a vapor-deposition process or like processes.

DESCRIPTION OF THE PREFERRED EMBODIMENTS

Hereinbelow, the present invention will be described in detail with reference to the accompanying drawings.

Figure 1:
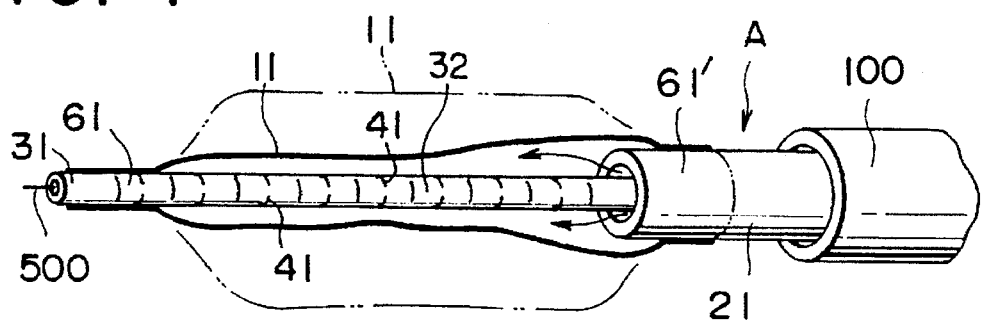
FIG. 1 is a perspective view of an essential part of a first embodiment of the dilatation catheter of the present invention.
Figure 2A:
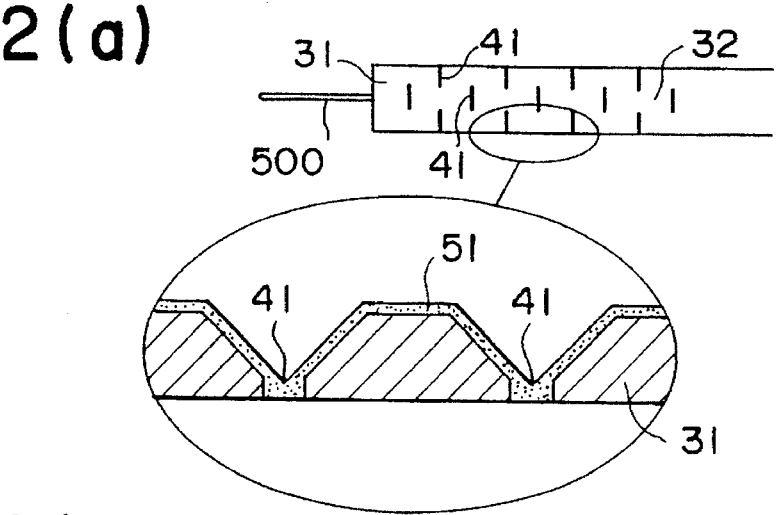
FIG. 2(a) is an enlarged sectional view of the circumferential grooves of the inner tube of the dilatation catheter of the present invention.
Figure 2B:
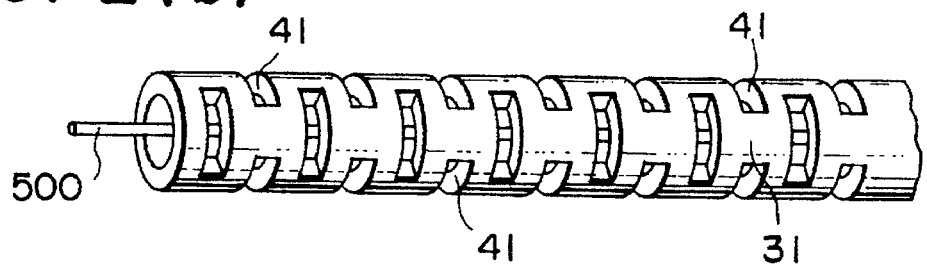
FIG. 2(b) is a perspective view of the inner tube of the dilatation catheter of the present invention shown in FIG. 2(a), illustrating the circumferential grooves of the inner tube.
Figure 3:
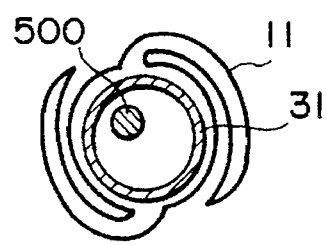
FIG. 3 is a cross-sectional view of the balloon and the inner tube of the dilation catheter of the present invention in a condition in which the balloon is wrapped around the inner tube under negative pressure.
Figure 4:
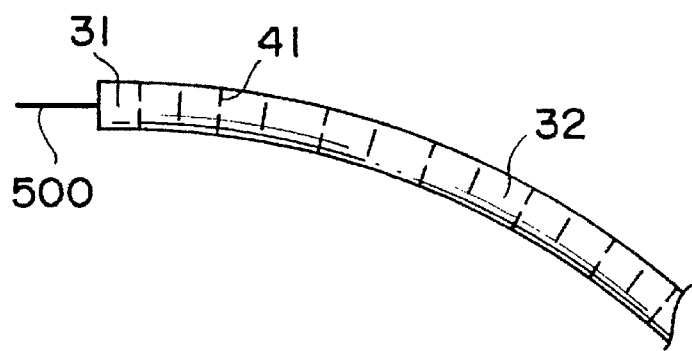
FIG. 4 is a side view of the inner tube of a second embodiment of the dilatation catheter of the present invention.
Figure 5:
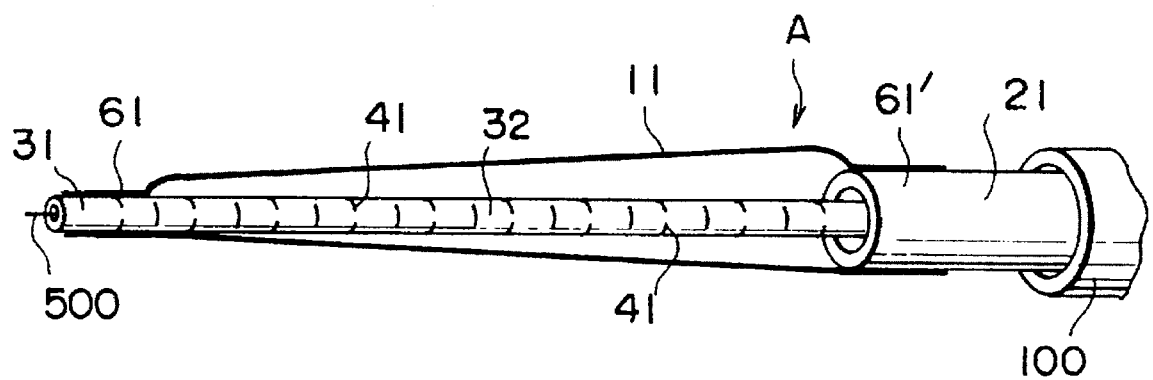
FIG. 5 is a perspective view of an essential part of a third embodiment of the dilatation catheter of the present invention.
Figure 6:
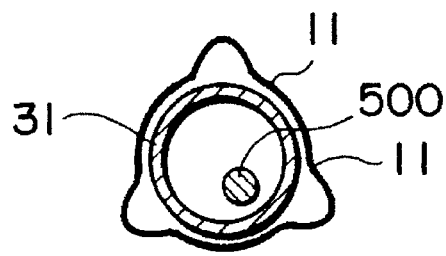
FIG. 6 is a cross-sectional view of the third embodiment of the dilatation catheter of the present invention shown in FIG. 5, illustrating the relationship between the balloon, inner tube and the guide wire.
Figure 7:
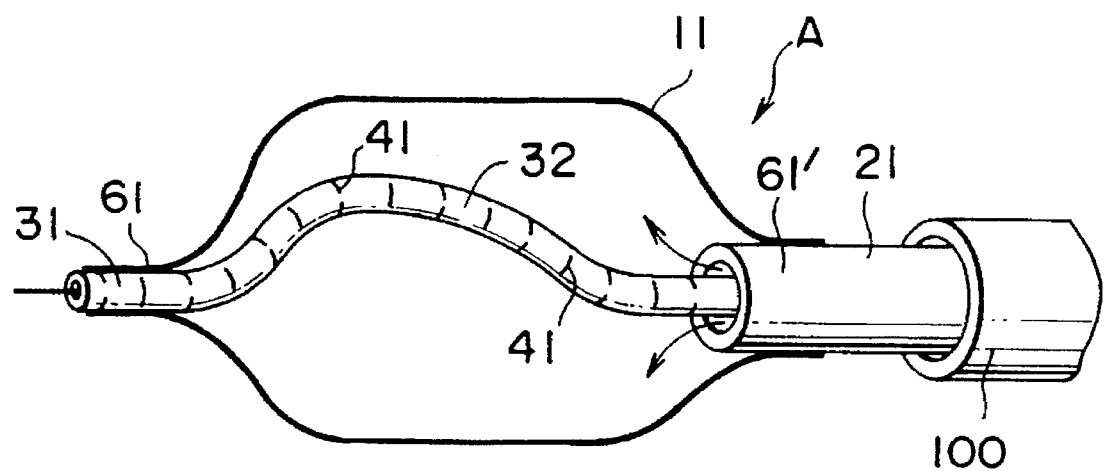
FIG. 7 is a perspective view of the essential part of the dilatation catheter of the present invention shown in FIG. 5 in a condition in which the balloon is inflated.

FIGS. 1 to 3 show a first embodiment of a dilatation catheter "A" of the present invention. FIG. 4 shows a second embodiment of the dilatation catheter "A". FIGS. 5 to 7 show a third embodiment of the dilatation catheter "A".

Figure 8A:
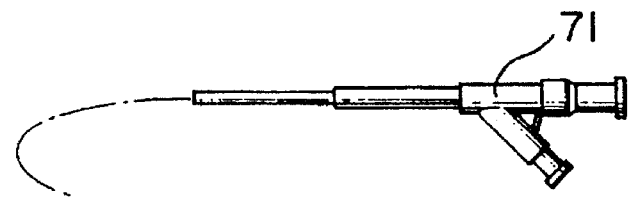
FIG. 8(a) is a schematic diagram illustrating the PTCA (i.e., percutaneous transluminal coronary angioplasty) operation in which the catheter assembly is introduced into the stenotic lesion of the coronary artery.
Figure 8A:
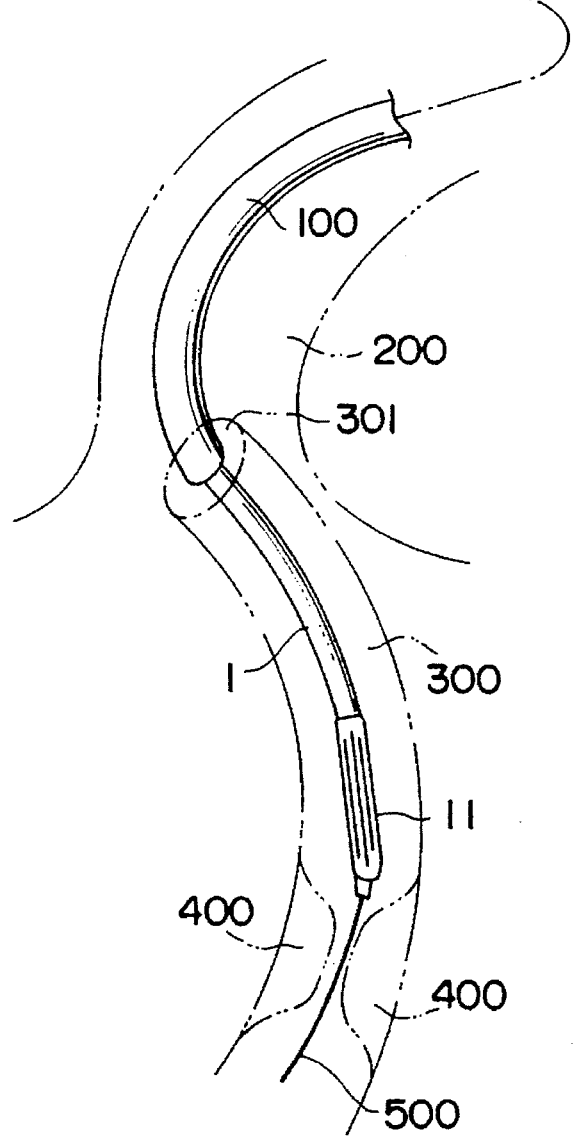

As is clear from FIGS. 1 and 8(a), in the dilatation catheter "A": an outer tube 21 is made of rigid plastics or metals (preferably stainless steels); an inner tube 31 is made of rigid plastics or metals (preferably stainless steels), and coaxially disposed inside the outer tube 21 to form a catheter assembly 1; a balloon 11 with a thin wall made of PE resins is mounted on a front-end portion of the catheter assembly 1 in a manner such that the balloon 11 has its front and its rear opening end fixedly mounted on an outer peripheral surface of a front-end portion of the inner tube 31 and that of a front-end portion of the outer tube 21 in a water-tight manner, respectively; and, a hub portion 71 is provided in a proximal end of the dilatation catheter "A".

Figure 8B:
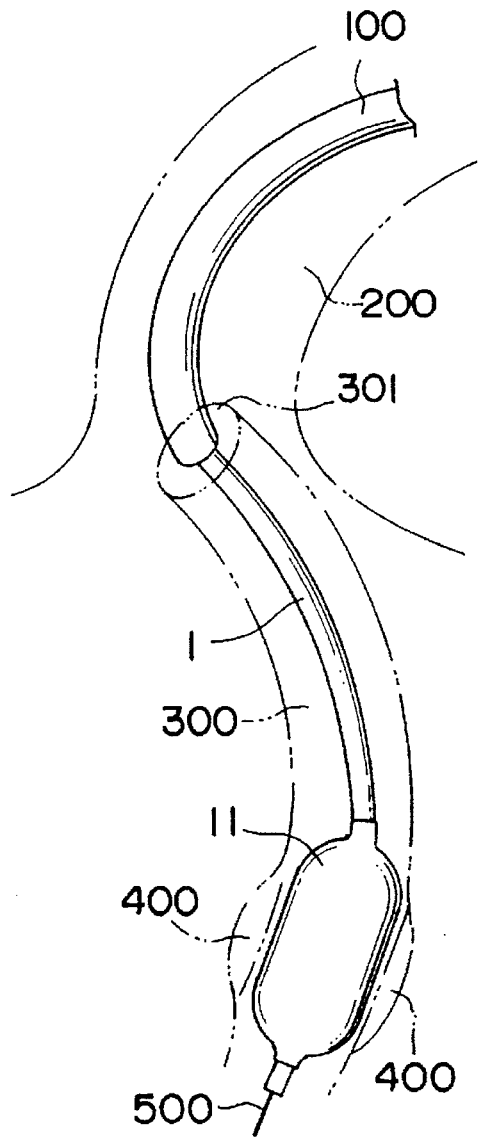
FIG. 8(b) is a schematic diagram illustrating the PTCA operation in which the balloon is inflated.

As shown in FIG. 8(a), in the catheter assembly 1, a guide wire 500 is inserted into the inner tube 31 and then passed through a stenotic lesion 400 (shown in phantom lines) of a coronary artery 300 (shown in phantom lines). After that, the balloon 11 is passed through a guiding catheter 100 and disposed in the stenotic lesion 400, the guiding catheter 100 being engaged with an inlet portion 301 (shown in phantom lines) of the coronary artery 300. Then, as shown in FIG. 8(b), a radiopaque dye (not shown) is supplied to the balloon 11 through a space defined between the inner tube 31 and the outer tube 21 to inflate the balloon 11 so that a passageway in the stenotic lesion 40 is enlarged in diameter.

As is clear from FIG. 1, in construction, the dilatation catheter "A" of the present invention has the inner tube 31 projected outward or forward from the outer tube 21. The balloon 11 with a thin wall made of PE (i.e., polyethylene) resins has its front and its rear opening end fixedly mounted on an outer peripheral surface of a front-end portion of the inner tube 31 and that of a front-end portion of the outer tube 21 in a water-tight manner to form a front fixed portion 61 and a rear fixed portion 61', respectively. A plurality of parallel-extending circumferential slits or grooves 41, each of which has a predetermined length, are provided to a distal area 32 having a certain length which extends from said front fixed portion 61 and over said rear fixed portion 61' in a direction of the hub portion in the inner tube 31.

The parallel-extending circumferential grooves 41 may be provided over the entire length of the inner tube 31, the grooves 41 being spaced apart from each other at predetermined axial intervals. It is possible to arbitrarily determine the number of the grooves 41 and their locations. These circumferential grooves 41 provided in the inner tube 31 enable the catheter assembly 1 to pass through both the guiding catheter 100 and the passageway of the stenotic lesion 400 in an easy manner.

The fixed portions 61, 61', which are formed on the outer peripheral surface of the front-end portion of each of the inner tube 31 and the outer tube 21 in a water-tight manner, are made of synthetic resins such as polyethylene and the like, and formed through a thermocompression bonding process, an ultrasonic bonding process, a vapor-deposition process or like processes.

Prior to its insertion into the guiding catheter 100, the balloon 11 is subjected to negative pressure as shown in FIG. 3. After that, the balloon 11 is inserted into the guiding catheter 100.

As shown in FIG. 2(a), some ones of the circumferential grooves 41 provided in the inner tube 31 may penetrate the wall of the inner tube 31. In case that the grooves 41 penetrate the wall of the inner tube 31, it is necessary to prevent the radiopaque dye from leaking in the inner tube 31 through such grooves 41. Consequently, as shown in FIG. 2(a), the outer peripheral surface of the inner tube 31 is coated with a synthetic resin 51 such as PE (i.e., polyethylene), PET (i.e., polyethylene terephthalate) and like resins, so that the radiopaque dye is prevented from leaking in the inner tube 31. The synthetic resin 51 may be formed into a heat shrinking tube being mounted on the inner tube 31.

In the dilatation catheter "A" of the present invention, the catheter assembly 1 is inserted into the guiding catheter 100 in a condition in which the guide wire 500 is inserted in the inner tube 31, as is in the conventional dilatation catheter. In operation, after the catheter assembly 1 is inserted into the guiding catheter 100, a front-end portion of the catheter assembly 1 is temporarily held in a position in front of the inlet portion 301 of the coronary artery 300. Under such circumstances, a doctor holding a proximal end (i.e., hub portion 71) of the dilatation catheter "A" repeatedly pushes and pulls the catheter assembly 1 so that the balloon 11 is positioned in the passageway in the stenotic lesion 400 of the coronary artery 300. Then, the radiopaque dye is supplied to the balloon 11 from an front-end opening portion of the outer tube 21 to inflate the balloon 11. The thus inflated balloon 11 exerts its expanding pressure on an inner wall of the passageway in the stenotic lesion 400 to increase such passageway in diameter, which permits a sufficient amount of the blood to pass through the passageway of the stenotic lesion 400 in the coronary artery 300.

In the above operation, even when a front end of the inner tube 31 hits the stenotic lesion 400 and the inner tube 31 is made of rigid plastics or metals (preferably stainless steels), there is no fear that the the inner tube 31 is permanently kinked or the balloon 11 is permanently bent to increase frictional resistance between the catheter assembly 1 and the coronary artery 300, since the circumferential grooves 41 are provided in the inner tube 31 to permit the distal area 32 of the inner tube 31 to resiliently change its curvature in the operation. Further, since the inner tube 31 provided with such circumferential grooves 41 is resiliently deformed along the guide wire 500, it is easy to position the balloon 11 in the passageway of the stenotic lesion 400 of the coronary artery 300 in the above operation.

In a second embodiment of the dilatation catheter of the present invention, in addition to the circumferential grooves 41, the distal area 32 of the inner tube 31 is provided with a slight curvature, which makes it easier to resiliently deform the inner tube 31.

Such slight curvature facilitates resilient deformation of the inner tube 31 without infecting the go-ahead properties of the inner tube 31 in operation, which makes it easier to position the balloon 11 in the passageway of the stenotic lesion 400 of the coronary artery 300.

Now, a third embodiment of the dilatation catheter of the present invention will be described. In this third embodiment, the balloon 11 is made of PET (i.e., polyethylene terephthalate) resins instead of PE (i.e., polyethylene) resins.

When the radiopaque dye filled in the balloon 11 is removed from the balloon 11, in contrast with the balloon 11 made of PE resins, the balloon 11 made of PET resins does not wrinkle, but assumes a flatfish-like shape with a width slightly larger than the diameter of the balloon 11 filled with the radiopaque dye, which prevents a smooth push and pull operation of the catheter assembly 1 in the coronary artery 300 to damage the coronary artery 300 and the stenotic lesion 400 thereof and sometimes makes it impossible to pull the catheter assembly 1 out of the guiding catheter 100 in operation. The balloon 11 made of PET resins in the third embodiment of the present invention has its front and its rear opening end fixedly mounted on an outer peripheral surface of a front-end portion of the inner tube 31 and that of a front-end portion of the outer tube 21 in a water-tight manner to form the front fixed portion 61 and the rear fixed portion 61', respectively, and the balloon is in a condition of axially stretched and fixed to said tubes.

Consequently, as is in the first embodiment of the dilation catheter of the present invention, in the third embodiment of the dilatation catheter "A" of the present invention, a plurality of parallel-extending circumferential grooves 41 are formed in a distal area 32 of the inner tube 31. If necessary, it is possible to provide a slight curvature in this area of the inner tube 31 as is in the second embodiment of the present invention. The circumferential grooves 41 may be provided over the entire length of the inner tube 31 at predetermined axial intervals.

The dilatation catheter "A" of the third embodiment of the present invention is operated in the same manner as that of the first embodiment to position the balloon 11 in the passageway of the stenotic lesion 400 of the coronary artery 300. In operation, there is no fear that the inner tube 31 is permanently kinked even when the front-end portion of the inner tube 31 hits against the stenotic lesion 400 of the coronary artery 300, because the circumferential grooves 41 are provided to the distal area 32 in the inner tube 31 to permit the inner tube 31 to resiliently change its shape and further the inner tube 31 is provided with a slight curvature if it is required. Consequently, it is possible for the third embodiment of the dilatation catheter "A" of the present invention to place the balloon 11 in the passageway of the stenotic lesion 400 in the coronary artery 300 as is in each of the first and the second embodiment of the present invention.

As shown in FIGS. 7 and 8(b), in the operation for widening in diameter the passageway of the stenotic lesion 400 in the coronary artery 300, when the radiopaque dye is filled in the balloon 11, the inner tube 31 is resiliently deformed or curved to facilitate expanding the balloon 11, which enables the balloon 11 to widen in diameter the passageway of the stenotic lesion 400 in the coronary artery 300 in an easy manner, as is in each of the first and the second embodiment of the present invention.

After completion of the above operation, when the radiopaque dye is removed from the balloon 11, the inner tube 31 returns to its straight shape under the influence of its resiliency. At the same time, the balloon 11 also returns to its initial shape or axially stretched shape with its initial small diameter, which reduces frictional resistance between the catheter assembly 1 and the guiding catheter 100 to facilitate pulling the catheter assembly 1 out of the guiding catheter 100.

In the third embodiment of the dilatation catheter "A" of the present invention, in a condition in which the balloon 11 is axially stretched, the balloon 11 had its front and its rear opening end fixedly mounted on an outer peripheral surface of a front-end portion of the inner tube 31 and that of a front-end portion of the outer tube 21 in a water tight manner to form a front and a rear fixed portion, respectively. Under such circumstances, if necessary, a suitable jig (not shown) is used to further reduce the diameter of the balloon 11.

What is claimed is:

1. In a dilatation catheter comprising:
   a balloon provided with a front and a rear opening end and a thin wall made of synthetic resins;

an outer tube;

an inner tube which is disposed inside said outer tube and has its tip portion projected outward from said outer tube;

a hub portion; and said balloon having said front and said rear opening end fixedly mounted in a water-tight manner on said inner tube and said outer tube to form a front and a rear fixed portion, respectively;

the improvement wherein:

a plurality of parallel-extending circumferential grooves are provided to a distal area of said inner tube, each of said circumferential grooves having a predetermined length, and said distal area having a certain length which extends from said front fixed portion and over said rear fixed portion in a direction of the hub portion.

2. The dilatation catheter as set forth in claim 1, wherein:

said parallel-extending circumferential grooves are provided also in the remaining area of said inner tube or also in said outer tube in addition to a distal area of said inner tube.

3. The dilatation catheter as set forth in claim 1, wherein:

said area of said inner tube assumes a slightly curved shape.

4. The dilatation catheter as set forth in claim 1, wherein:

each of said inner tube and said outer tube is made of metals or rigid plastics which are not kinked.

5. The dilatation catheter as set forth in claim 1, wherein:

a pair of said parallel-extending circumferential grooves are oppositely disposed from each other on the same diameter.

6. A dilatation catheter comprising:

a balloon provided with a front and a rear opening end and a thin wall made of polyethylene terephthalate resins;

an outer tube;

an inner tube which is disposed inside said outer tube and has its tip portion projected outward from said outer tube;

a hub portion;

said balloon having said front and said rear opening end fixedly mounted in a water-tight manner on said inner tube and said outer tube in a condition in which said balloon is axially stretched to form a front and a rear fixed portion, respectively; and a plurality of parallel-extending circumferential grooves provided to a distal area of said inner tube, each of said circumferential grooves having a predetermined length, and said distal area having a certain length which extends from said front fixed portion and over said rear fixed portion in a direction of the hub portion.

7. The dilatation catheter as set forth in claim 6, wherein:

said parallel-extending circumferential grooves are provided also in the remaining area of said inner tube or also in said outer tube in addition to a distal area of said inner tube.

8. The dilatation catheter as set forth in claim 6, wherein:

said area of said inner tube assumes a slightly curved shape.

9. The dilatation catheter as set forth in claim 6, wherein:

each of said inner tube and said outer tube is made of metals or rigid plastics which are not kinked.

10. The dilatation catheter as set forth in claim 6, wherein:

a pair of said parallel-extending circumferential grooves are oppositely disposed from each other on the same diameter.

* * * * *